(12) United States Patent
Knott et al.

(10) Patent No.: US 10,016,924 B2
(45) Date of Patent: Jul. 10, 2018

(54) METHOD FOR STERILISING PLASTIC CONTAINERS HAVING A PROTECTION DEVICE

(71) Applicant: KRONES AG, Neutraubling (DE)

(72) Inventors: Josef Knott, Walkenstetten/Schierling (DE); Guenter Frankenberger, Koefering (DE); Hans Scheuren, Regensburg (DE)

(73) Assignee: KRONES AG, Neutraubling (DE)

( * ) Notice: Subject to any disclaimer, the term of this patent is extended or adjusted under 35 U.S.C. 154(b) by 237 days.

(21) Appl. No.: 14/725,232

(22) Filed: May 29, 2015

(65) Prior Publication Data

US 2015/0258728 A1 Sep. 17, 2015

Related U.S. Application Data

(62) Division of application No. 13/584,424, filed on Aug. 13, 2012, now abandoned.

(30) Foreign Application Priority Data

Aug. 19, 2011 (DE) .................. 10 2011 052 862

(51) Int. Cl.
*A61L 2/08* (2006.01)
*B29C 49/42* (2006.01)
*B65B 55/08* (2006.01)
*B29C 49/10* (2006.01)

(52) U.S. Cl.
CPC ............ *B29C 49/4252* (2013.01); *A61L 2/08* (2013.01); *A61L 2/087* (2013.01); *B65B 55/08* (2013.01); *A61L 2202/23* (2013.01); *B29C 49/10* (2013.01)

(58) Field of Classification Search
CPC ....................................................... A61L 2/087
USPC ............................................................ 422/22
See application file for complete search history.

(56) References Cited

U.S. PATENT DOCUMENTS

| 4,835,425 | A | 5/1989 | LaSota |
| 9,302,896 | B2 | 4/2016 | Drenguis et al. |
| 2007/0193652 | A1* | 8/2007 | Till ............... B67C 7/0073 141/144 |
| 2010/0054987 | A1 | 3/2010 | Krueger et al. |
| 2010/0209290 | A1 | 8/2010 | Cirri et al. |
| 2011/0012030 | A1 | 1/2011 | Bufano et al. |

(Continued)

FOREIGN PATENT DOCUMENTS

| JP | 2007-125119 | 5/2007 |
| WO | 2011011079 A1 | 1/2011 |

OTHER PUBLICATIONS

Japanese Office Action from Japanese Patent Application No. 2012-174048, dated May 6, 2016.

*Primary Examiner* — Donald R Spamer
(74) *Attorney, Agent, or Firm* — Greer, Burns & Crain, Ltd.

(57) ABSTRACT

A method for operating an apparatus for sterilizing containers where the containers are each held and are transported along a predefined path by means of a movable carrier, and a plurality of sterilization units are arranged on the carrier, each having rod-like bodies that are introduced into the containers and apply charge carriers onto an internal wall of the containers. The charge carriers exit through an exit window of the rod-like bodies, as the charge carriers move in a longitudinal direction relative to the rod-like bodies.

16 Claims, 1 Drawing Sheet

(56) References Cited

U.S. PATENT DOCUMENTS

2011/0012032 A1 1/2011 Bufano et al.
2011/0016829 A1 1/2011 Drenguis et al.
2012/0219455 A1 8/2012 Meinzinger et al.
2012/0273694 A1 11/2012 Lejeune et al.
2013/0001434 A1 1/2013 Lejeune et al.

* cited by examiner

U.S. Patent Jul. 10, 2018 US 10,016,924 B2
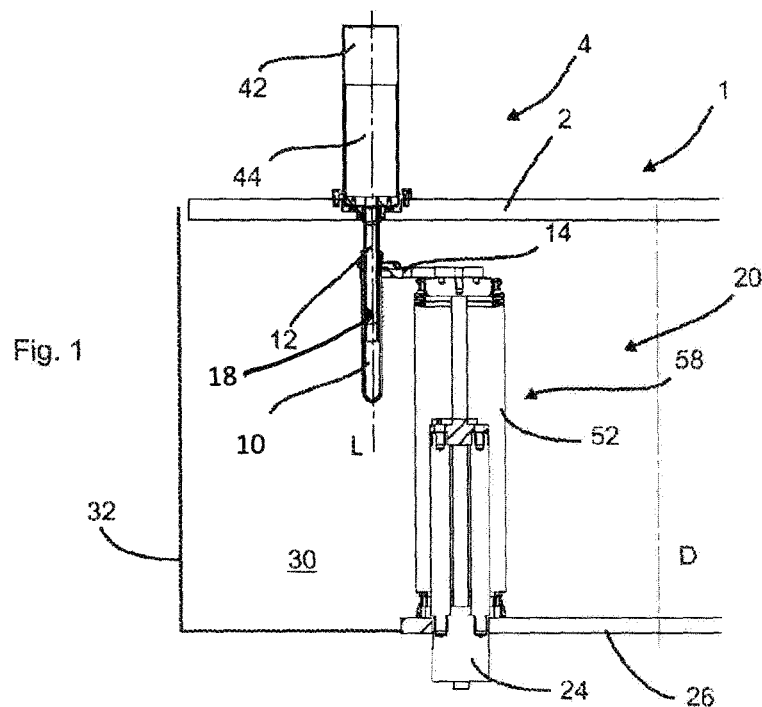
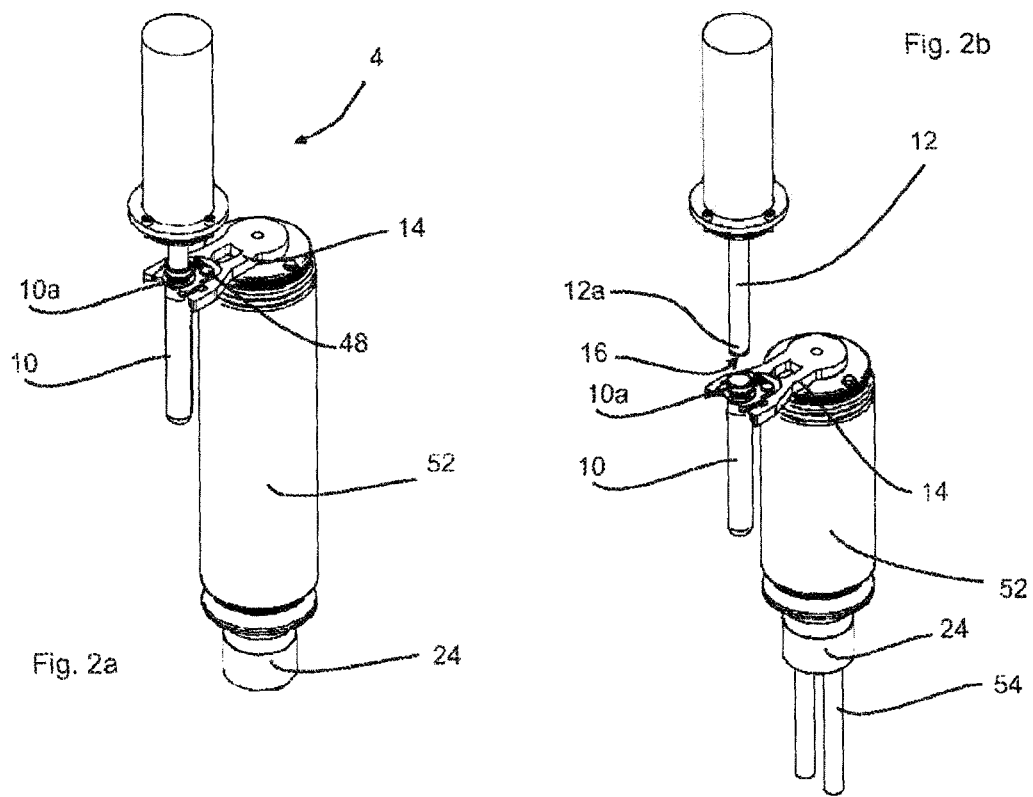

METHOD FOR STERILISING PLASTIC CONTAINERS HAVING A PROTECTION DEVICE

PRIORITY CLAIM

This application is a divisional application of and claims the benefit of U.S. patent application Ser. No. 13/584,424 filed on Aug. 13, 2012, which claims priority to and the benefit of German Patent Application No. 10 2011 052 862.8 filed on Aug. 19, 2011.

BACKGROUND

The present invention relates to an apparatus and a method for sterilising containers and in particular plastic containers. Various methods for sterilising containers are known from the prior art. So for example, it is known to apply a liquid and/or gaseous medium such as for example $H_2O_2$ to containers. Apart from that, also apparatus and methods have recently become known, wherein radiation and/or charge carriers has/have been applied to the containers for the purpose of sterilisation. In doing so, it is possible to insert a beam finger into the inside of the containers and to irradiate this container from the inside with charge carriers and in particular with electrons. These beam fingers have to be designed to be relatively delicate and/or respectively thin-walled so as to ensure on the one hand that the finger can be inserted through the mouth into the inside of the container and on the other hand to enable also the required high electron accelerations to be achieved. Further, such apparatus often include also cooling devices for cooling an exit window for the charge carriers.

As a result of the above, such sterilisation devices are very sensitive for example to contamination or aggressive cleaning agents, but in particular to shocks. In practice, therefore, breakdowns and failures often occur for example as a result of knocks against these beam fingers, in particular during cleaning or maintenance operations.

SUMMARY

The present invention is therefore based on the object of providing an apparatus and a method that provide improved protection of the apparatus for sterilising the containers.

An apparatus according to the invention for sterilising containers includes a movable carrier, on which a plurality of sterilisation units are arranged, wherein each sterilisation unit has a source of radiation or respectively a radiation emitting device and/or a charge carrier source, as well as a rod-like body that is designed such that it can be inserted into the inner space of the container through a mouth. Further, an exit window is provided on the rod-like body, through which the charge carriers can exit. Further, a plurality of holding units for holding the containers are provided, said holding units being movable relative to the rod-like body in a longitudinal direction of the rod-like bodies.

According to the invention, the apparatus includes a protection device to ensure that the rod-like bodies are arranged at least partially within protective bodies in a specified mode of operation.

The invention will be described below with reference to charge carrier emitters and in particular to electron emitters. Due to the high sensitivity of such charge carrier emitters, the invention is particularly advantageous also for this purpose. However, it is to be noted that the invention can also be applied to different radiation emitting devices such as in particular UV lamps, X-ray emitters or radioactive emitters, which can in particular be inserted into the containers.

It is therefore proposed that in at least one mode of the apparatus, special protective measures for protecting in particular the rod-like bodies, but also for example the exit window are taken. In particular, therefore, protection for the beam fingers during cleaning and sterilisation operations of the system is to be provided. It is therefore proposed to move or traverse during these operations for example corresponding containers over the rod-like bodies to be protected.

A mode is in particular understood to mean a mode of operation of the apparatus, but it is not necessary that containers are sterilised during this mode of operation. For example, also the repair of the system or the cleaning thereof can be understood to be such a mode. However, this will preferably be a mode in which at least one drive of the apparatus can be activated, such as for example a drive that can effect a lifting or lowering movement of the holding unit. Also, assembly and disassembly operations of parts of the apparatus may be carried out within such a mode, however, the assembly, i.e. the (initial) installation of the entire system in particular is not regarded as a mode of operation in terms of the invention.

As mentioned above, the rod-like bodies can be moved relative to the holding devices or respectively relative to the containers held by these holding devices. In this context it is possible for the holding devices to be movable in the longitudinal direction of the containers, however it would also be possible for the rod-like bodies themselves to be moved and also for both the rod-like bodies and the holding devices to be moved. The charge carriers are in particular electrons.

In a further advantageous method, all of the rod-like bodies are respectively moved into the protective bodies in said mode. Advantageously, the protective bodies completely surround at least the exit window and particularly preferably they are terminated towards the bottom or towards the end of the rod-like bodies.

However, it is also possible and preferable for the protective bodies to surround a large part of the rod-like body and preferably the entire rod-like body in the circumferential direction thereof. Preferably, the protective bodies surround the rod-like body over at least 30% of the length thereof, preferably over at least 50% of the length thereof, preferably over at least 70% of the length thereof and particularly preferably over at least 90% of the length thereof.

In a further advantageous embodiment, the rod-like bodies are provided on a carrier. The term protection means will hereinafter be understood to mean the entire unit including the protective bodies and any movement mechanisms for the protective bodies. Advantageously, exactly one protective body, for example a protective cover, is provided on each rod-like body in said mode. Advantageously, once the rod-like body has been moved into the protective body, an axis of symmetry of the rod-like body coincides with an axis of symmetry of the protective body.

In this mode, in particular also those rod-like bodies are provided with protective bodies or are respectively moved into them, which in said mode are in positions in which no containers are present during working operation. Such positions may for example be positions between an outlet star wheel and an inlet star wheel of the sterilisation apparatus.

In a further advantageous embodiment, the protection means include a movement mechanism for moving the protective bodies in the longitudinal direction of the rod-like bodies, which ensures that the rod-like bodies have at least partially been inserted into the protective body in the specified mode. Advantageously, as mentioned above, all of the rod-like bodies have respectively been inserted into the protective bodies partially and preferably in the same way. This may again be a movement mechanism that moves the protective bodies in the longitudinal direction of the containers and in doing so pushes them for example over the rod-like bodies. However, it would also be conceivable for the movement mechanism to move the rod-like bodies themselves or respectively to move itself into the protective bodies.

In a further advantageous embodiment, the carrier is a rotatable carrier. In this embodiment, therefore, the apparatus is a rotary machine.

In a further advantageous embodiment, the protective bodies are arranged relative to the rod-like bodies in the specified mode of operation in a contact-free manner. In this way it can be achieved that any damage to the rod-like bodies will be avoided also during the insertion operation of the rod-like bodies into the protective bodies.

In a further advantageous embodiment, the apparatus includes a cleaning unit for cleaning the apparatus. This cleaning unit may here include for example a plurality of jet nozzles which apply a cleaning medium onto the apparatus or onto parts of the apparatus. Thus, for example, stationary cleaning nozzles may be provided and the individual cleaning units or sterilisation units may move relative to these nozzles so as to be cleaned.

Apart from that, the apparatus may also include a sterilisation unit for sterilising the apparatus itself. Also the sterilisation process may here be carried out by means of cleaning media, however, it would also be conceivable for the sterilisation process again to be carried out by irradiation, such as by means of UV irradiation or electron irradiation.

In a further advantageous embodiment, each sterilisation unit has at least one electric motor drive unit for moving the gripping elements relative to the rod-like bodies and/or for moving the protective bodies relative to the rod-like bodies in the longitudinal direction of the rod-like bodies. In the prior art, cam rollers or respectively stationary cams are usually used for moving such beam fingers.

However, in the case of the apparatus according to the invention it is desired, for example during a cleaning operation, to insert several and preferably all of the beam fingers—and in particular independently from the rotary position of the carrier—into their protective bodies. In this case therefore, a unitary movement or orientation of all the protective bodies is advantageous in this cleaning mode. It is therefore proposed to decouple the movements of the individual protective bodies relative to the beam fingers from each other. In other words, the electric motor drives (e.g. linear motors and/or servomotors) ensure in particular an independent movement of the individual gripping elements or respectively even of the protective bodies relative to the rod-like bodies. However, also pneumatic and/or hydraulic drives may be considered for use as drives.

In a further advantageous embodiment, the protective device ensures that the containers to be sterilised serve as protective bodies. In this embodiment it is provided that no additional protective bodies are present, but that the containers which are sterilised during working operation serve as protective bodies at the same time. These containers are relatively suitable because the rod-like bodies have to be moved into them anyway. To this end it is possible, for example in the cleaning mode, to move the containers, i.e. bottles or preforms, over the rod-like bodies or the beam fingers. Advantageously during this time, any emission of radiation or any emission of charge carriers will be interrupted.

In a further advantageous embodiment, the apparatus includes at least one stabilisation unit in order to fix or respectively sterilise the protective bodies relative to the rod-like bodies. Thus, for example, a stop may be provided on which the containers come to rest. In this way it can be achieved that not even a somewhat harder knock against the protective body will cause any damage to the beam fingers.

However, it would also be possible to provide a holder for stabilising the containers for example from below.

The present invention is further directed to a method for operating an apparatus for sterilising containers and in particular plastic containers. Here, the containers to be sterilised are respectively held and are transported along a predefined path by means of a movable carrier. Here, a plurality of sterilisation units arranged on the carrier may be provided, each of which have rod-like bodies that are inserted into these containers through a mouth and that apply charge carriers and/or radiation onto an internal wall of the containers. In this process, these charge carriers and/or radiation exits through an exit window of the rod-like body and a relative movement of the containers occurs in a longitudinal direction of the rod-like bodies relative to the rod-like bodies, in order to insert the rod-like bodies into the containers.

According to the invention, in a further mode of the apparatus, the rod-like bodies are each inserted into protective bodies which at least partially surround said bodies, and this insertion is also carried out by way of a relative movement between the protective bodies and the rod-like bodies in a longitudinal direction of the rod-like bodies.

As mentioned above, the radiation may be a radiation of charge carriers, but there may also be other types of radiation such as UV radiation. In the case of UV radiation, the exit window may be chosen to be considerably larger than in the case of an electron emitter and may for example completely surround the UV light source.

This insertion of the rod-like bodies into the protective body is performed in particular in order to carry out a cleaning operation. Advantageously, the rod-like bodies are here moved into the containers to be sterilised. However, it would also be possible to provide additional bodies such as for example additional protective covers.

In a further advantageous method, all of the rod-like bodies are moved into the protective bodies substantially by the same distance during said mode, which may for example be a cleaning mode. This means that in this case protective bodies are also provided in positions in which they are not present during working operation, such as for example in the circumferential direction between an outlet star wheel and an inlet star wheel of the carrier.

Advantageously therefore, each sterilisation unit is equipped with a protective body.

Advantageously in one method step, the apparatus is equipped with protective bodies and particularly preferably each sterilisation unit is equipped with a protective body. However, this is in particular carried out automatically. It would also be possible to equip initially each sterilisation unit with a container prior to a cleaning operation and to insert the respective beam finger or respectively rod-like body into this container.

In a preferred method, two consecutive cleaning and/or sterilisation processes are carried out in said mode.

One process can be carried out as follows:

after completion of the production process, each rod-like body is moved into a protective body preferably by means of the respective lifting mechanism. This protective body may be a special protection shape, the container or a preform. Contrary to the production operation, however, here all of the rod-like bodies are arranged in a protective body.

Subsequently, the system is powered down, for example temporarily stopped. In a further method step, the system can be opened in order to carry out a cleaning operation. After this, the system is preferably manually cleaned. In a further step, the system may be closed (in particular using a safety protocol). Finally, an automatic sterilisation of the system may be carried out and the production process may finally be resumed.

In a further advantageous embodiment, therefore, the apparatus also includes a clean room, into which the containers to be sterilised are passed. This clean room can here advantageously surround the transport path of the containers in a channel-like manner. This means that the sterilisation of the containers is also carried out under sterile conditions.

It would further also be conceivable for at least one wall of the above-mentioned rotatable carrier to form at the same time a wall of this clean room.

BRIEF DESCRIPTION OF THE DRAWINGS

Further advantages and embodiments will become evident from the attached figures, wherein:

FIG. 1 shows a schematic view of an apparatus according to the invention.

FIG. 2a shows a sterilization unit moved into a container.

FIG. 2b shows the sterilization unit of FIG. 2a moved out of the container.

DETAILED DESCRIPTION

FIG. 1 shows a partially schematic view of an apparatus 1 according to the invention for sterilising containers 10. In the embodiment shown in FIG. 1, the containers are plastic preforms 10, the inner walls of which are to be sterilised here. The apparatus 1 according to the invention may be followed by further units within the context of a container treatment system, such as for example a stretch blow moulding machine that expands the plastic preforms into containers, a heating unit for heating the plastic preforms and the like. However, it would also be possible to use the apparatus according to the invention for sterilising containers and in particular plastic containers.

A plurality of sterilisation units, which are in their entirety identified with 4, is provided on a rotatable carrier 2, however, only one of these sterilisation units 4 is shown. These sterilisation units 4 move together with the plastic containers to be sterilised.

Each of the sterilisation units 4 includes a source of charge carriers 42, which may in particular be an electron source. Reference numeral 44 identifies an acceleration unit that accelerates the charge carriers or respectively electrons in the direction of and also through a rod-like body 12. An exit window (not shown) is provided at the bottom end of this rod-like body 12, through which the accelerated electrons can exit.

Apart from that, the sterilisation units preferably include deflecting units (not shown), which direct or steer the charge carriers also onto a lateral inner wall of the plastic containers.

Reference numeral 14 identifies a holding unit such as a gripping clamp that is used for holding the plastic preforms 10 during the sterilisation process. This holding unit 14 is here movable in the longitudinal direction L of the plastic containers 10, in order to insert in this way the rod-like bodies 12 into the inside of the plastic containers 10 through a mouth of the plastic containers 10. A corresponding drive unit 24, which is here implemented as an electric motor, in particular a linear motor, effects the movement of the holding units 14 relative to the rod-like bodies 12.

These drive units 24 are here also provided on a carrier 26, wherein this carrier 26 rotates—like the carrier 2—about the rotary axis D.

Reference numeral 30 identifies a clean room, within which the plastic containers are sterilised. This room is here delimited by the carrier 2, the carrier 26 and two further walls (not shown). Here, in particular also a stationary outer wall 32 may be provided which is only schematically shown in FIG. 1 and which delimits the clean room 30 towards the outside. Advantageously, this outer wall 32 is arranged to be stationary, whereas the remaining walls delimiting the clean room 30 move or rotate about the rotary axis D.

In a further advantageous embodiment, at least one sealing unit (not shown) is provided which seals these walls that are movable relative to each other. An example of such a sealing unit would be a so-called surge tank. However, it would also be possible for the entire apparatus 1 to be located within a clean room. It would also be conceivable for the apparatus not to be located within a clean room, for example if only a pre-sterilisation operation of the plastic containers is to be carried out.

In the embodiment shown in the figures, the plastic containers to be sterilised are used at the same time as protective bodies 18. Thus, for example within the context of a cleaning and/or sterilisation operation, the rod-like bodies 12 can be moved into the plastic preforms. Preferably, however, the protective bodies generally include a cavity into which the rod-like bodies can be inserted. Advantageously the protective bodies, with the exception of the opening through which the respective rod-like body 12 is inserted, have no further openings either. However, it would also be conceivable for the protective bodies to have an opening at the bottom end thereof, through which a cleaning medium (that is to be applied for example onto the rod-like bodies 12) can be discharged. Reference numeral 20 identifies in its entirety the protection unit for protecting the rod-like bodies 12.

FIGS. 2a and 2b show two illustrations of an apparatus according to the invention. In the situation shown in FIG. 2a, the rod-like bodies 12 have been moved into the plastic preform 10, so that the system can be cleaned without any risk of damage to the rod-like bodies 12. Here again, what can be seen is the mouth 10a of the containers, through which the rod-like bodies are inserted into the container 10 or the protective body 18.

Reference numeral 16 relates to an exit window, through which the electrons can exit from the rod-like body 12 or respectively the beam finger 12. This exit window is provided in an end section 12a of the rod-like body 10. Advantageously, also a cooling unit for cooling the exit window is provided, and for this purpose a corresponding coolant may be passed for example between an outer housing of the rod-like body and an inner housing located within this rod-like housing.

Reference numeral 48 schematically identifies a stabilisation unit. In the situation shown in FIG. 2a, this stabilisation unit 48 may be moved up to a stabilisation unit (not shown) that may be formed to be complementary, for example on the carrier 2, in order to stabilise in this way the protective body 18 relative to the carrier. This stabilisation unit 48 may be generally implemented in such a way that it effects a stabilisation relative to the carrier 2 or generally relative to an element, on which also the rod-like body 12 is fixedly mounted.

In this way, a relative movement between the protective body 18 and the rod-like body 12 may be prevented during the cleaning operation. However, it would also be possible for the holding unit 14 to be stabilised relative to its movement unit. Also, additional stabilisation units (not shown) may be provided, which support the container on a base body below the mouth, such as for example a second gripping element that is provided below the holding unit 14 in the longitudinal direction L. In this way, the containers are held in two different positions along the longitudinal direction thereof, as a result of which an enhanced stabilisation of the container 10 is achieved.

The drive unit 24, which during working operation is used to move the rod-like bodies into the plastic containers 10, is also used during the cleaning operation to move the rod-like bodies 12 into the protective bodies 18 thereof. To this end it would be possible to insert all of the rod-like bodies 12 of the respective sterilisation units into the plastic preforms or respectively the plastic containers and to move them preferably into an upper position as shown in FIG. 2a.

Preferably, each sterilisation unit 4 also has such a drive unit 24, and these drive units can advantageously be controlled independently from each other. Advantageously, also the holding or gripping units 14 can be controlled in particular between a closed condition, in which they hold the containers 10, and an open condition, in which they release the containers 10.

In order to initiate the above-mentioned cleaning mode, it is possible for each of these gripping units to be occupied by a plastic container 10 acting as a protective body 18.

This could also be done via a corresponding control of an outlet star wheel that carries off the plastic containers from the apparatus during working operation. Once a cleaning operation has been carried out, the individual holding units 14 with the plastic containers 10/18 arranged thereon can be lowered down again and the respective plastic containers 10 can be moved out of the apparatus. Advantageously, the containers are transferred out and/or discarded, and such a transferring out is advantageously carried out automatically.

It would also be possible to use special protective bodies which are inserted into the apparatus in particular for cleaning purposes and which can preferably be reused after cleaning. Advantageously, such protective bodies are designed in such a way that they can be gripped by the holding units 14. Such protective bodies 18 may here be dimensioned such that the risk of any damage to the individual rod-like bodies is reduced even further, for example by providing them with a diameter that is markedly larger than the diameter of the rod-like bodies.

Reference numeral 52 identifies a cover unit that covers the movement mechanism for lifting and lowering the holding unit. This cover unit may for example be a set of bellows. This cover unit is here advantageously provided within the clean room 30 or respectively forms itself a border of the clean room 30. Part of the cover can also be a housing on which preferably an additional set of bellows is provided so as to enable a lifting and lowering movement.

Within the cover unit, a lifting and lowering mechanism 58 for lifting and lowering the holding unit may be provided, which is driven by the drive unit 24 (and thus preferably from outside of the clean room).

This lifting and lowering mechanism may here include holding rods 54 which are moved by the drive unit 24.

It would also be possible for the holding or gripping units for the plastic containers 10 to be suitable for gripping other protective bodies, for example by way of the gripping units allowing the reception of objects having cross sections that are larger than the cross sections of the containers 10 to be sterilised.

However, it would also be possible that protective bodies are already provided on the apparatus, which protective bodies are moved over the rod-like bodies, for example by means of a separate lifting mechanism. Also, the protective bodies may be formed as shields which only partially surround the rod-like bodies. The protection apparatus according to the invention is also suitable for protecting for example rod-like UV lamps which can be inserted into containers for treating such containers.

The applicant reserves the right to claim all of the features mentioned in the application documents as being essential to the invention in as far as they are novel over the prior art either alone or in combination with other features.

What is claimed is:

1. A method for operating an apparatus for sterilizing containers, the method comprising:
   holding and transporting each of the containers to be sterilized along a predefined path by a movable carrier, wherein a plurality of sterilization units are arranged on the carrier, and each of the sterilization units has rod bodies that are moved into the containers through a mouth of the containers using a first lifting mechanism and apply charge carriers onto an internal wall of the containers, wherein the charge carriers exit through an exit window of the rod bodies, and wherein a relative movement of the containers in a longitudinal direction of the rod bodies relative to the rod bodies is carried out by said first lifting mechanism so as to insert the rod bodies into the containers; and
   automatically positioning protective bodies over said rod bodies using a second lifting mechanism, in a further mode of the apparatus, such that said protective bodies at least partially surround said rod bodies, wherein the positioning of said protective bodies is also carried out by relative movement between the protective bodies and the rod bodies in a longitudinal direction of the rod bodies.

2. The method as claimed in claim 1, wherein a working operation being a mode during which the rod bodies are introduced into the containers through a mouth of the containers and apply charge carriers onto an internal wall so as to sterilize the inner wall each of the containers, thereby the working operation being a different mode from the further mode.

3. The method as claimed in claim 1, wherein the further mode is one of a repair mode, a cleaning mode or a mode in which an assembly or a disassembly of parts is performed.

4. The method as claimed in claim 1, wherein protective bodies are also arranged in positions in which no containers are present during working operation.

5. The method as claimed in claim 1, wherein the protective bodies are arranged in a circumferential direction between an outlet star wheel and an inlet star wheel of the carrier.

6. The method as claimed in claim 1, wherein at least one of the protective bodies and the containers are preforms.

7. The method as claimed in claim 1, wherein at least one of said first lifting mechanism and said second lifting mechanism includes at least one electric motor drive unit for moving said at least one first lifting mechanism and said second lifting mechanism.

8. The method as claimed in claim 7, wherein said at least one electric motor drive unit causes said first lifting mechanism to move the rod bodies into the plastic containers during a working operation and causes said second lifting mechanism to move the rod bodies into the protective bodies during a cleaning operation.

9. The method as claimed in claim 1, wherein all of the rod bodies are inserted into the protective bodies in this further mode.

10. The method as claimed in claim 1, wherein two consecutive cleaning or sterilization processes are carried out in the further mode.

11. The method as claimed in claim 1, wherein second lifting mechanism includes a movement mechanism for moving the protective bodies in the longitudinal direction of the rod bodies, which second lifting mechanism causes the rod bodies to be at least partially inserted into the protective bodies in the further mode.

12. The method as claimed in claim 1, wherein the carrier is a rotatable carrier.

13. The method as claimed in claim 1, wherein in the further mode of operation, the protective bodies are arranged in a contact-free manner relative to the rod bodies.

14. The method as claimed in claim 1, wherein the apparatus includes a cleaning unit for cleaning the apparatus.

15. The method as claimed in claim 1, wherein the containers to be sterilized serve as the protective bodies.

16. The method as claimed in claim 1, wherein the apparatus has at least one stabilization unit in order to fix the protective bodies relative to the rod bodies.

* * * * *